United States Patent [19]
Seaton et al.

[11] Patent Number: 5,853,667
[45] Date of Patent: *Dec. 29, 1998

[54] TEST SAMPLE POSITIONING SYSTEM

[75] Inventors: William Ernest Seaton, Chesterfield; Mark Joseph Fanning, Florissant; Craig Drager, Ballwin; Ron Robinson, Bridgeton; Roger James Morris, St. Louis, all of Mo.; Jean-Pierre Bernard Gayral, Amberieu en Bugey, France; JoAnne T. Gerst, St. Louis, Mo.

[73] Assignee: bioMérieux Vitek, Inc., Hazelwood, Mo.

[*] Notice: The term of this patent shall not extend beyond the expiration date of Pat. No. 5,736,102.

[21] Appl. No.: 934,934

[22] Filed: Sep. 22, 1997

Related U.S. Application Data

[63] Continuation of Ser. No. 604,725, Feb. 21, 1996, Pat. No. 5,736,102.

[51] Int. Cl.$^6$ .................................................. G01N 35/04
[52] U.S. Cl. ............................ 422/65; 422/63; 422/104; 436/43; 436/47; 198/465.2; 198/468.11; 198/746; 198/748
[58] Field of Search .................................. 622/63, 65, 99, 622/100, 104; 436/63, 47; 198/465.2, 468.11, 748, 746

[56] References Cited

U.S. PATENT DOCUMENTS

| | | |
|---|---|---|
| 3,221,781 | 12/1965 | Forsstrom . |
| 3,478,859 | 11/1969 | Krempel et al. . |
| 3,895,528 | 7/1975 | Luitwieler, Jr. et al. . |
| 4,147,250 | 4/1979 | Schulz . |
| 4,236,825 | 12/1980 | Gilford et al. . |
| 4,265,855 | 5/1981 | Mandle et al. . |
| 4,454,939 | 6/1984 | Kampf et al. . |
| 4,632,808 | 12/1986 | Yamamoto et al. . |
| 4,673,657 | 6/1987 | Christian . |
| 4,699,583 | 10/1987 | Grigoli et al. . |
| 4,710,352 | 12/1987 | Slater et al. . |
| 4,711,851 | 12/1987 | McNamara et al. . |
| 4,861,554 | 8/1989 | Sakuma . |
| 4,890,930 | 1/1990 | Nohso . |
| 5,008,082 | 4/1991 | Shaw . |
| 5,192,506 | 3/1993 | Kureshy et al. . |
| 5,232,665 | 8/1993 | Burkovich et al. . |
| 5,270,006 | 12/1993 | Uchigaki et al. . |
| 5,350,052 | 9/1994 | Gebald et al. . |
| 5,370,215 | 12/1994 | Markin et al. . |
| 5,374,395 | 12/1994 | Robinson et al. . |
| 5,384,094 | 1/1995 | Schacher . |
| 5,417,922 | 5/1995 | Markin et al. . |

*Primary Examiner*—Long V. Le
*Attorney, Agent, or Firm*—McDonnell Boehnen Hulbert & Berghoff

[57] ABSTRACT

A positioning system for a sample testing machine incudes a base pan and a set of independent drive systems for sliding a sample tray across the base pan. Each of the drive systems incudes a paddle that engages a side of the sample tray. The paddle is slideably mounted to a shaft with a collar that slides over the shaft. A motor and drive belt is provided to move the collar along the shaft, causing the paddle to engage the side of the sample tray and slide the sample tray across the base pan. Track sections are provided in the base pan to prevent the sample tray from rotating as the paddle slides the sample tray across the base pan.

6 Claims, 10 Drawing Sheets

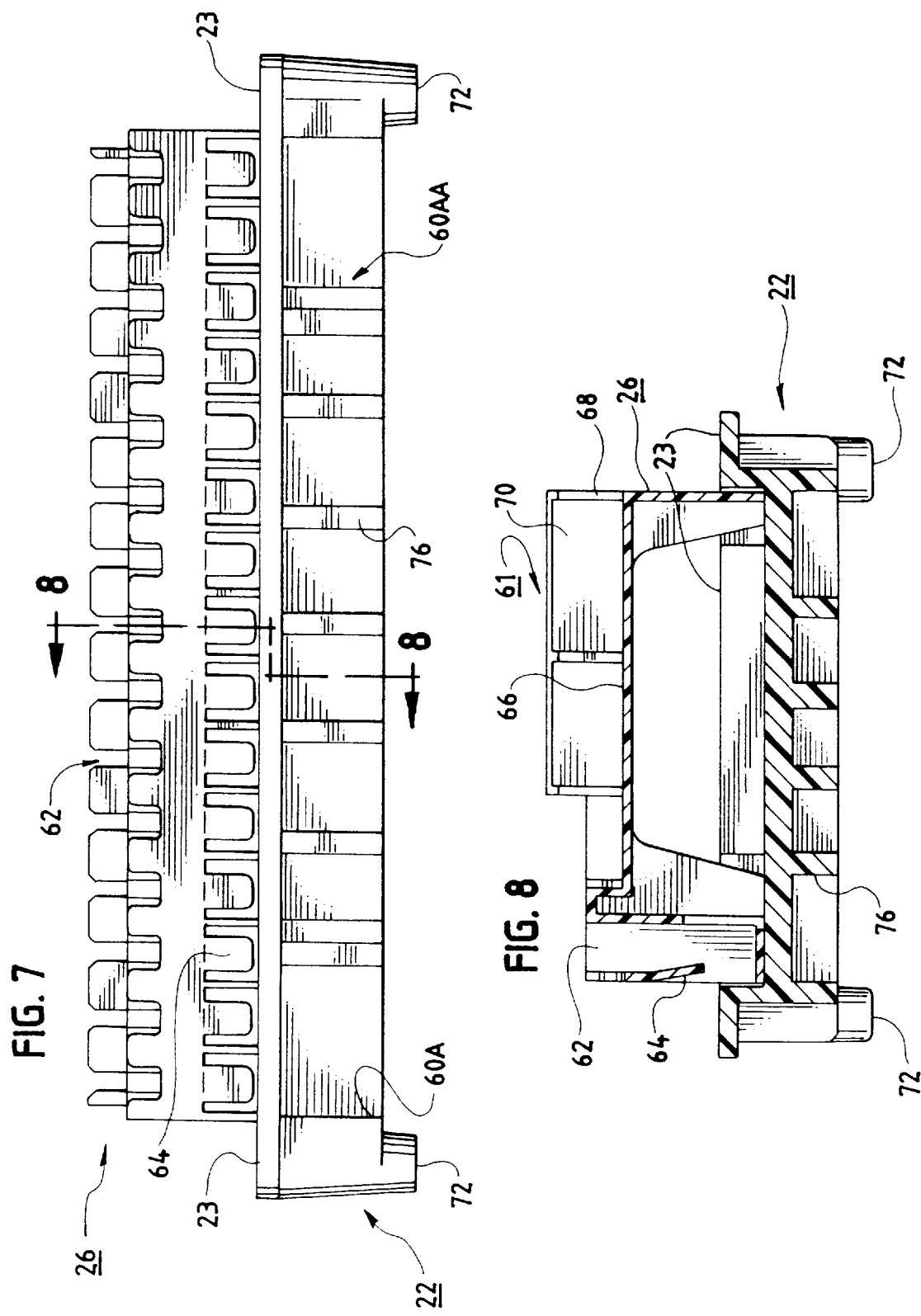

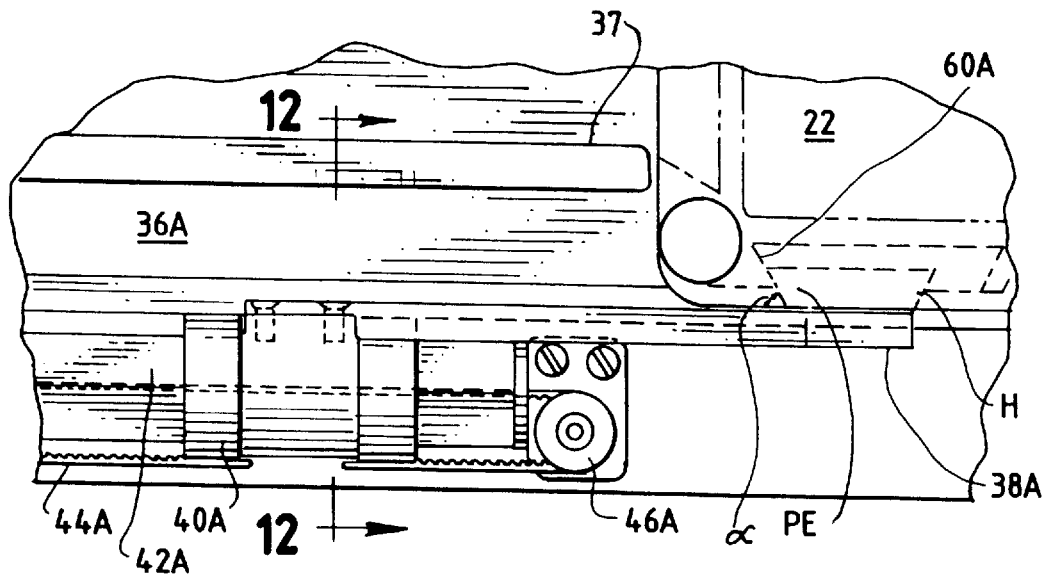
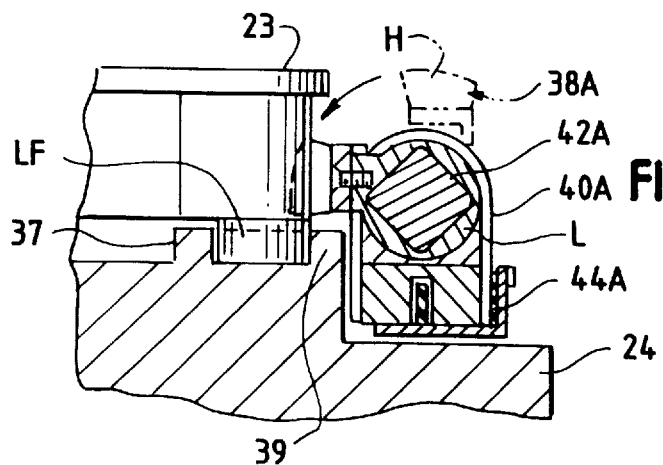
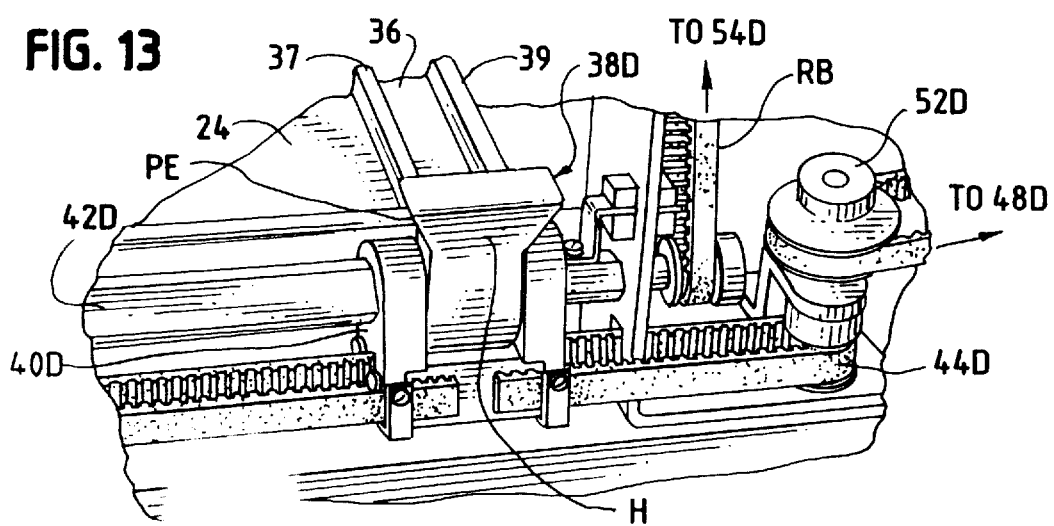

TEST SAMPLE POSITIONING SYSTEM

This is a continuation of application Ser. No. 08/604,725, filed Feb. 21, 1996, now U.S. Pat. No. 5,736,102.

BACKGROUND OF THE INVENTION

A. Field of the Invention

This invention relates to systems and methods for moving a test sample or group of test samples to various stations of a machine, such as a biological sample testing machine.

B. Description of Related Art

Biological samples can be subject to chemical or optical analysis using various techniques, one of which is transmittance and/or fluorescence optical analysis. The purpose of the analysis may be to identify an unknown biological agent in the sample, test the sample to determine the concentration of a substance in the sample, or determine whether the biological agent is susceptible to certain antibiotics, as well as the concentration of antibiotics that would be effective in treating an infection caused by the agent.

A technique has been developed for conducting optical analysis of biological samples that involves the use of a sealed test sample card containing a plurality of small sample wells. Typically, during manufacture of the cards e.g. for microbiological analysis, the wells are filled with either various types of growth media for various biological agents, or else various concentrations of different antibiotics. The cards have an internal fluid passageway structure for allowing fluid to enter the wells of the card through a transfer tube port, and an integral transfer tube extending outwardly from the transfer tube port. The prior art method involved the manual insertion of one end of the transfer tube into the card and the other end into a test tube, and then the manual placement of the card with attached transfer tube and test tube into a vacuum filling and sealing machine, such as the Vitek® Filler Sealer. The filling and sealing machine generates a vacuum, causing the fluid in the test tube to be drawn into the wells of the sample card.

After the wells of the card are loaded with the sample, the cards are manually inserted into a slot in a sealer module in the machine, where the transfer tube is cut and melted, sealing the interior of the card. The cards are then manually removed from the filler/sealer module and loaded in a column fashion into a reading and incubating machine, such as the VITEK® Reader. The reading and incubating machine incubates the cards at an incubation temperature, and has an optical assembly that moves up and down relative to the cards to read the wells of the cards.

This arrangement has limitations, in that two machines are required to process and analyze the cards. Furthermore, additional time and labor are required to conduct the complete analysis of the card.

To combine the several functions of biological sample processing and optical reading into a single automatic sample processing and reading machine poses substantial challenges. One particularly difficult challenge is to provide a positioning system to move the samples about the machine from station to station. The present invention provides a positioning system that is reliable, precise in its positioning of the samples, and that is suitable for the varied types of operations performed on automated sample testing equipment such as test sample cards.

Representative prior art test sample positioning systems for use in biological and immunoassay analyzer machines are described in U.S. Pat. No. 4,265,855 to Mandle et al., U.S. Pat. No. 5,232,665 to Burkovich et al., U.S. Pat. No. 4,890,930 to Nohso, U.S. Pat. No. 4,710,352 to Slater et al., U.S. Pat. No. 4,632,808 to Yamamoto et al., and U.S. Pat. No. 4,236,825 to Gilford. These systems tend to either have unnecessary complexity in their mechanical components or involve drive and transport systems that are unsuitable to the processing of test sample cards and the associated test tubes. The system described in the above-cited Mandle et al. patent discloses a drive pin arrangement for moving a set of blocks carrying test tubes about an immunochemical analysis machine. The machine is fully loaded with blocks positioned in front and rear rows, with a vacant spot for one block at opposite corners of the machine. Drive pins then move simultaneously to push one block from the front row to the vacant spot on the back row, and one block from the back row to a vacant spot on the front row. The blocks are then advanced one space along the length of the front and rear rows, and the process repeats. The functioning of this drive system is dependent on the machine being filled with blocks, and hence lacks flexibility. Further, in order for one block to be moved through all the stations of the machine, the blocks in front of it must first be cycled through the stations around the machine.

The present invention overcomes the disadvantages of the prior art positioning systems by providing an efficient test sample positioning system for that is suitable for biological and chemical sample testing machines. It provides independent drive systems that can simultaneously transport a number of trays loaded with samples independently, permitting processing by the various stations of the trays at the same time, without the delays and complexities found in many prior art systems. The invention further permits the performance of the functions of loading sample fluids into the cards and reading of the cards in a single machine automatically and without human intervention, thus achieving a significant advance in the art. These and other objects, advantages and features of the invention will become more apparent from the following detailed description of a preferred embodiment of the invention.

SUMMARY OF THE INVENTION

A positioning system is provided for moving a test sample tray across a base pan to various stations of a sample testing machine. The system comprises a set of independent drive systems which operate to move the sample tray independently from each other. Each of the drive systems includes a paddle that engages the side of the sample tray. The paddle is mounted to a collar that is moveable along a rotatable shaft by a drive motor and drive belt subassembly. As the drive motor and drive belt subassembly moves the collar along the shaft, the paddle pulls the sample tray across the base pan. Preferably, the drive systems also include a shaft rotation motor for rotating the shaft such that the paddle is rotatable into and out of engagement with the sample tray.

The base pan may be given a rectangular shape, in which case four independent drive systems may be provided, enabling the tray to be moved along all four of the sides of the base pan. By making the drive systems operable independently from each other, the positioning system allows for a plurality of sample trays to be moved about the machine at the same time.

The base pan is preferably provided with a set of track sections defined by a set of raised ridges and a raised rim of the base pan. The track sections prevent the boat from undergoing any rotational motion as the boat is pulled by the drive systems along the base pan. The track sections have a set of slots to permit the feet of the sample tray to pass through the track sections as the sample tray is moved sequentially in perpendicular directions across the base pan.

BRIEF DESCRIPTION OF THE DRAWINGS

Presently preferred embodiments of the invention are depicted in the drawings, wherein like reference numerals refer to like elements in the various views, and wherein:

FIG. 7 is a side view of the cassette and boat of FIG. 6;

FIG. 8 is a sectional view of the cassette and boat of FIG. 7 along the lines 8—8;

FIG. 11 is a detailed top view of the paddle 38A engaging the boat 22;

FIG. 12 is a sectional view of the paddle and collar of FIG. 11; and

FIG. 13 is a perspective view of the fourth drive assembly of FIG. 3, showing the fourth paddle 38D and other components of the assembly.

DETAILED DESCRIPTION OF THE PREFERRED EMBODIMENT

Overview of Preferred Test Sample Machine

Figure 1:
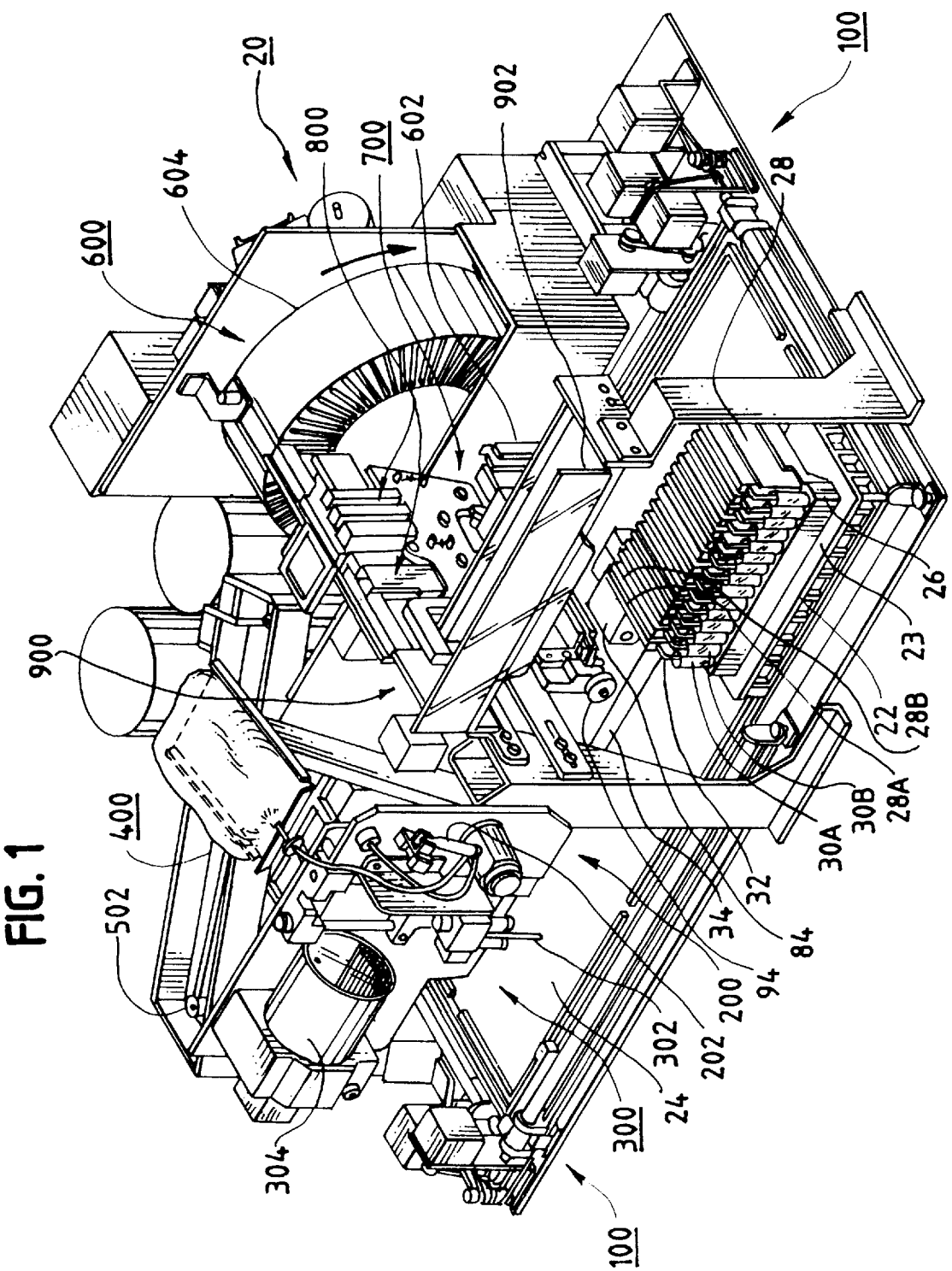
FIG. 1 is a perspective view of a preferred automatic biological sample testing machine that incorporates the test sample positioning system of the present invention.

FIG. 1 is a perspective view of a preferred biological sample testing machine 20. The following detailed description of the preferred embodiment of the inventive optical reader and sample card transport systems will be discussed in the context of the biological sample testing machine 20. It will be appreciated, however, that the principles of the invention may be used in other types of testing machines besides the preferred biological sample testing machine 20. Other possible implementations include chemical testing, immunochemistry, immunodiagnostic, and nucleic acid probe assay machines.

The biological sample testing machine 20 includes a biological test sample positioning system 100 having four independent motor-driven paddles, which is designed to pull a sample tray 22 (referred to herein as a "boat") across a base pan 24 around the machine 20 to several discrete stations, where various operations are performed on the samples in the boat 22. Prior to the start of the procedure, a technician loads a cassette 26 with a plurality of test cards 28 and receptacles such as test tubes 30 containing biological or control samples to be tested. Each test card 28 has an L-shaped transfer tube 32 protruding therefrom for permitting the fluids containing biological samples to be drawn from the test tubes 30 into the wells of the test cards 28. The technician places the loaded cassette 26 into the boat 22 at a loading station for the machine, such as the front, right hand corner of the base pan 24 shown in FIG. 1. The combined boat 22 and loaded cassette 26 are then moved as a unit over the surface of the base pan 24 about the machine 20 by the test sample positioning system 100.

In a typical microbiological testing scenario, described below for purposes of illustration but not limitation, the test cards 28 come in two varieties: (1) identification cards, in which particular different growth media are placed in the wells of the card 28 when the cards are manufactured, and (2) susceptibility cards, in which different concentrations of different antibiotics are placed in the wells of the card 28. The identification cards are used to identify the particular unknown biological agent present in the sample. The susceptibility cards are used to determine the susceptibility of the biological agent to various concentrations of antibiotics or other drugs. In the test procedure described below, identification and susceptibility tests can be performed on a single sample in one cycle of operation of the machine 20. To accomplish this, the cassette 26 is loaded such that a test tube 30A containing a biological sample, connected via a transfer tube 32 to an identification card 28A, is placed adjacent to a test tube 30B connected via a transfer tube 32 to a susceptibility card 28B. Alternate test cards may be provided for other types of biological or chemical testing, such cards incorporating various test reagents.

The cards 28 preferably contain bar codes across the top of the card for reading by a bar code reader built into the machine 20. The bar codes are unique to each card, and identify card information such as card type, expiration date, and serial number, and are used to correlate test data and/or results from the cards with the patient and the biological sample. In addition, the entire boat or cassette may have sample information for all of the cards loaded in the cassette stored on a memory device affixed to the cassette 26, such as a memory button or "touch button" available from Dallas Semiconductor Corp., 4401 S. Beltwood Parkway, Dallas Tex.

In the representative example shown in FIG. 1, seven or eight of the test tubes 30 in the boat 22 contain biological samples, and are in fluid communication with identification cards 28 by the straw-like transfer tube 32. The biological sample test tube 30A and its associated identification card 28A can be thought of as a set. The biological sample test tubes and identification cards are typically arranged in an alternating pattern in the cassette 26. Each biological sample test tube 30A and identification card 28A set is adjacent to an empty test tube 30B placed in communication with a susceptibility card 28B via a transfer tube 32. It will be appreciated that the cards and associated test tubes could be ordered in any order in the cassette 26 depending on the particular testing requirements for the samples. For example, the cards could be arranged as follows: identification (ID), susceptibility (SU), ID, ID, ID, SU, SU, ID, SU . . . Further examples would be all identification cards and all susceptibility cards.

After the loaded cassette 26 is installed at the loading station on to the boat 22, the test sample positioning system 100 operates to move the boat 22 over the base pan past a station 84 (FIG. 1) for achieving cassette information stored in touch buttons applied to the rear of the cassette 26. The test sample positioning system 100 then operates to move the boat 22 and cassette 26 past a bar code reading station for reading bar codes applied to the tops of the cards. As the cassette passes by the wheel 94, the wheel 94 rocks the cards 28 backwards slightly so that the bar codes can be read by an optical bar code reader. The reader (not shown) is mounted to the center mount 34 above and slightly forward of the wheel 94.

The test sample positioning system 100 operates to move the boat 22 and cassette 26 over the base pan 24 to a diluting station 200. The diluting station contains a rotating shot tube 202, by which a predetermined volume of diluent (such as saline solution) is added to the empty susceptibility test tubes in the cassette 26, e.g. test tube 30B. As the leading edge of the boat 22 is moved to the left during this process, it passes under a pipetting station 300. The pipetting station 300 includes a mechanism that automatically removes a pipette 302 from a source of pipettes 304, lowers the pipette 302 into the biological sample test tube 30A, and removes with vacuum a predetermined volume of biological fluid from the biological sample test tube 30A using the pipette 302. The pipetting and diluting stations are described in further detail in U.S. Pat. No. 5,698,409 issued to Bishop et al., assigned to the assignee of the invention which is incorporated by reference herein.

The test sample positioning system 100 then moves the boat 22 to the left by an amount equal to the separation distance in the Cassette 26 between adjacent test tubes 30A and 30B, e.g. 15 mm. The pipetting station 300 then lowers the pipette 302 containing the biological fluid from the biological sample test tube 30A into the adjacent susceptibility test tube 30B (having already received a quantity of diluent from the diluting station 200), expels the fluid into the test tube 30B, and drops the pipette 302 into the susceptibility test tube 30B. The process of movement of the boat 22 by the test sample positioning system 100, adding diluent to the susceptibility test tubes 30B at the diluting station 200, and transferring of biological samples from the biological sample test tubes 30A to the adjacent susceptibility test tubes 30B at the pipetting station 300, continues until all of the identification and/or susceptibility test tubes sets (if any) in the boat 22 have been so processed. By virtue of the close spacing of the pipetting station 300 and the diluting station 200, simultaneous diluting and pipetting operations can be performed on multiple test tubes in a single boat 22. After the last pipetting operation has been performed, the test sample positioning system 100 then moves the boat all the way to the left-hand edge of the base pan 24.

It will be understood by persons skilled in the art that the cassette 26 may be loaded entirely with biological samples in the test tubes 30 and identification cards 28, such as the case where a batch of biological samples are to be tested to identify the contents of the samples. In this example, the diluting and pipetting operations are not necessary. However, in other types of sample testing, other diluents or fluids may be added to or withdrawn from the test tubes. In the example of where no diluting or pipetting operations are performed (e.g., where the pipetting and diluting operations were performed off-line), the cassette 26 is loaded with test tubes and cards, and the positioning system 100 would simply move the boat 22 and loaded cassette 26 directly past the diluting station 200 and the pipetting station 300 without stopping, all the way to the left hand edge of the base pan 24.

Once at the left hand edge of the base pan 24, the test sample positioning system 100 operates to move the boat 22 along the left hand edge to a vacuum station 400. The vacuum station 400 is seen better in FIG. 2, which is a perspective view of the machine 20 with the diluting station 200 and the pipetting station 300 removed. At the vacuum station 400, a vacuum chamber 402 is lowered onto the boat 22 such that the bottom surface of the vacuum chamber 402 sealingly engages the top peripheral surface 23 of the boat 22. Vacuum is applied to the chamber 402 under microprocessor control, causing air in the interior of the test sample cards 28 to evacuate out of their associated test tubes and to be withdrawn from the chamber 402. The vacuum cycle is precisely managed to optimize filling using a closed loop servo system to regulate the change of vacuum and timing of the complete cycle. After a predetermined dwell period, the chamber 402 is vented gradually to atmosphere under microprocessor control. The venting of the cards causes the fluid in the test tubes 30 to be drawn into the cards 28, filling the wells in the cards 28.

Figure 2:
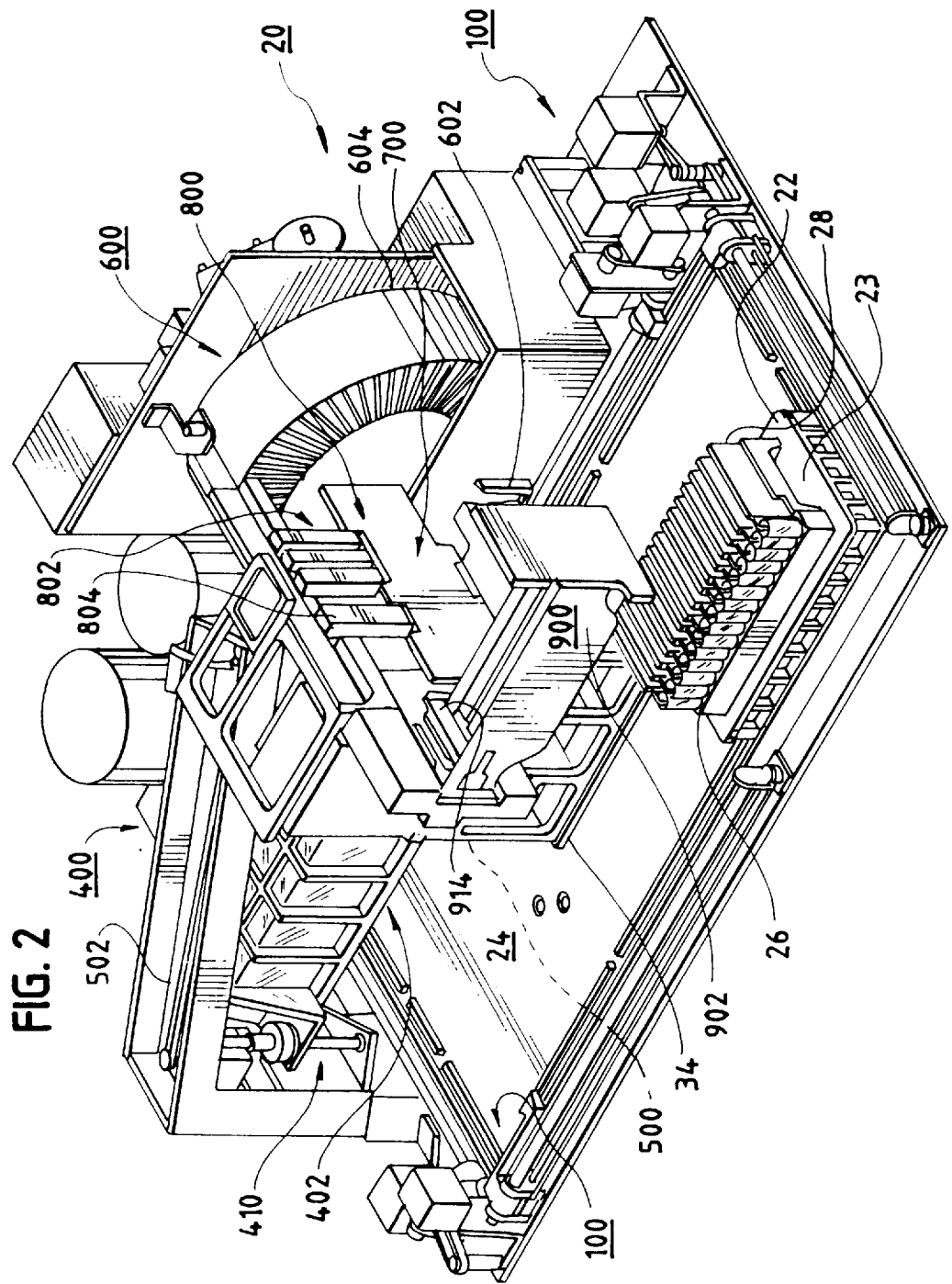
FIG. 2 is a perspective view of the machine of FIG. 1, with the diluting and pipetting stations removed to better illustrate the vacuum station of the machine.

The test sample positioning system 100 then operates to advance the boat 22 to the right across the rear of the base pan 24 to a cut and seal station 500, located behind the center mount 34 in FIGS. 1 and 2. The cut and seal station 500 consists of a hot cutting wire and attached support plate (not shown), and a drive mechanism 502 that lowers the cutting wire and support plate to the same elevation as the top portion of the transfer tubes 32 adjacent to where the transfer tubes 32 enter the test cards 28. As the boat 22 is advanced past the cut and seal station 500, the transfer tubes 32 are forced past the hot cutting wire. With the assistance of fore and aft constraints placed on the movement of the cards 28 by the walls of the cassette 26, and the lateral constraints on the movement of the card 28 by the cassette and wall structures of the machine 20, the hot cutting wire cuts the transfer tubes 32 by melting of the transfer tube material as the boat 22 is advanced past the hot cutting wire. A small stub of transfer tube material is left on the exterior of the card 28. The stub seals the interior of the card 28 from the atmosphere.

The test sample positioning system 100 then advances the boat 22 across the rear of the base pan 24 behind the center mount 34 to a carousel incubation station 600. A reciprocating cam driver is mounted to the center mount 34 opposite a slot 602 that pushes the cards off the cassette 26 one at a time through the slot 602 into a carousel 604. The carousel 604 is housed in an enclosure that is maintained at an appropriate incubation temperature for the particular assay, for example, 35 degrees C. The enclosure is not fully shown in FIGS. 1 and 2 in order to show the carousel 604. The carousel 604 is rotated in synchronism with the movement of the boat 22 over the rear of the base pan 24 by the test sample positioning system 100, so as to place the next slot in the carousel 604 in line with the slot 602 opposite the next card in the cassette 26. If the carousel 604 is only going to be partially loaded with cards, it may be advisable to load the cards into every other slot a slot or two periodically in order to balance out the weight distribution in the carousel 604. For example, where the carousel has 60 slots and only 30 cards are to be processed, the cards are loaded into every other slot.

After all of the cards 28 have been loaded into the slots of the carousel 604, the boat 22 is advanced along the right hand edge of the base pan 24 back to its starting position (shown in FIGS. 1 and 2) for removal of the cassette 26 (containing the test tubes and transfer tubes remnants) and receipt of a new cassette. Alternatively, the boat 22 could be moved to an exit station located, for example, in the rear or right hand side of the base pan 24.

As the cards 28 are being incubated in the incubation station 600, the cards are periodically, sequentially pushed out of the slots of the carousel 604 at the top of the carousel 604 by a reciprocating cam driver, one at a time, and moved by an optical scanner transport station 700 past a fluorescence and transmittance optics station 800. The wells of the card 28 are selectively subject to transmittance and/or fluorescence optical testing by the transmittance and fluorescence optics station 800. The transmittance and fluorescence optics station 800 includes detectors and processing circuitry to generate transmittance and fluorescence data for the wells in the cards 28, and to report the data to a central processing unit for the machine 22. If the test is not complete, the transport station 700 moves the card 28 back into its slot in the carousel 604 for more incubation and additional reading.

Typically, each card will be read every 15 minutes as the carousel makes one revolution. Typical incubation times for the cards 28 are on the order of two to eighteen hours, consisting of roughly four transmittance and fluorescence data sets per hour for each of the wells in the card 28 subject to the optical analysis.

After the testing is complete, the cards are moved by the optical scanner transport system 700 into a card output station 900 shown in FIG. 1. The card output station 900 consists of a detachable magazine 902 that is placed to the side of the optical station 800 at approximately the same elevation as the optical station 800. The technician removes the magazine 902 from the machine 20 as needed or when the tray is full of cards, empties the cards into a suitable biohazard disposal unit, and replaces the magazine 902 back into the machine 20.

Test Sample Positioning System 100 Detailed Description

Figure 3:
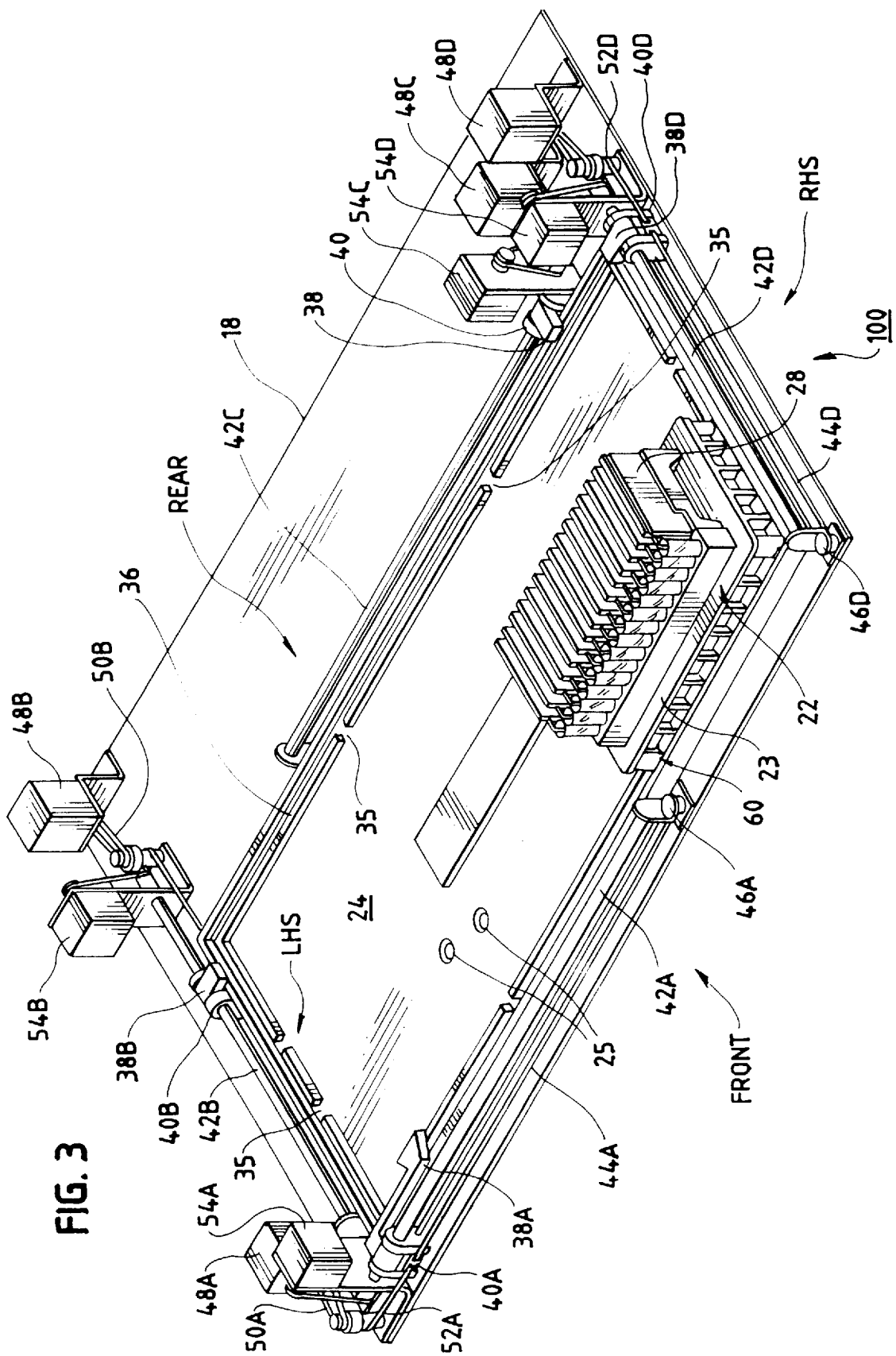
FIG. 3 is a detailed perspective view of the test sample positioning system of FIGS. 1 and 2.

Referring now in particular to FIG. 3, the test sample positioning system 100 will be described in detail. The system 100 is shown in a perspective view in FIG. 3, with all of the stations mounted to the center mount 34 (such as the pipetting station 300) and the incubation station 600 removed in order to more clearly illustrate the components of the positioning system 100.

The system 100 has a base pan 24 mounted to a table support structure 18, across which the boat 22 is slid from station to station in the machine 20. The base pan 24 in the preferred embodiment is of rectangular shape having four sides at right angles to each other: a front side, a left hand side (LHS), a rear side, and a right hand side (RHS). The four sides of the base pan 24 allow the boat 22 to be moved clockwise in a loop about the machine back to its starting position at a loading station (the position of the boat 22 and cassette 26 shown in FIGS. 1–3) after all of the operations on the sample card 28 have been completed. However, the inventive principles of the test sample positioning system are applicable to other geometries for a base pan 24. Additionally, the paddles and motors are capable of moving the boat 22 in a counter-clockwise direction.

Figure 4:
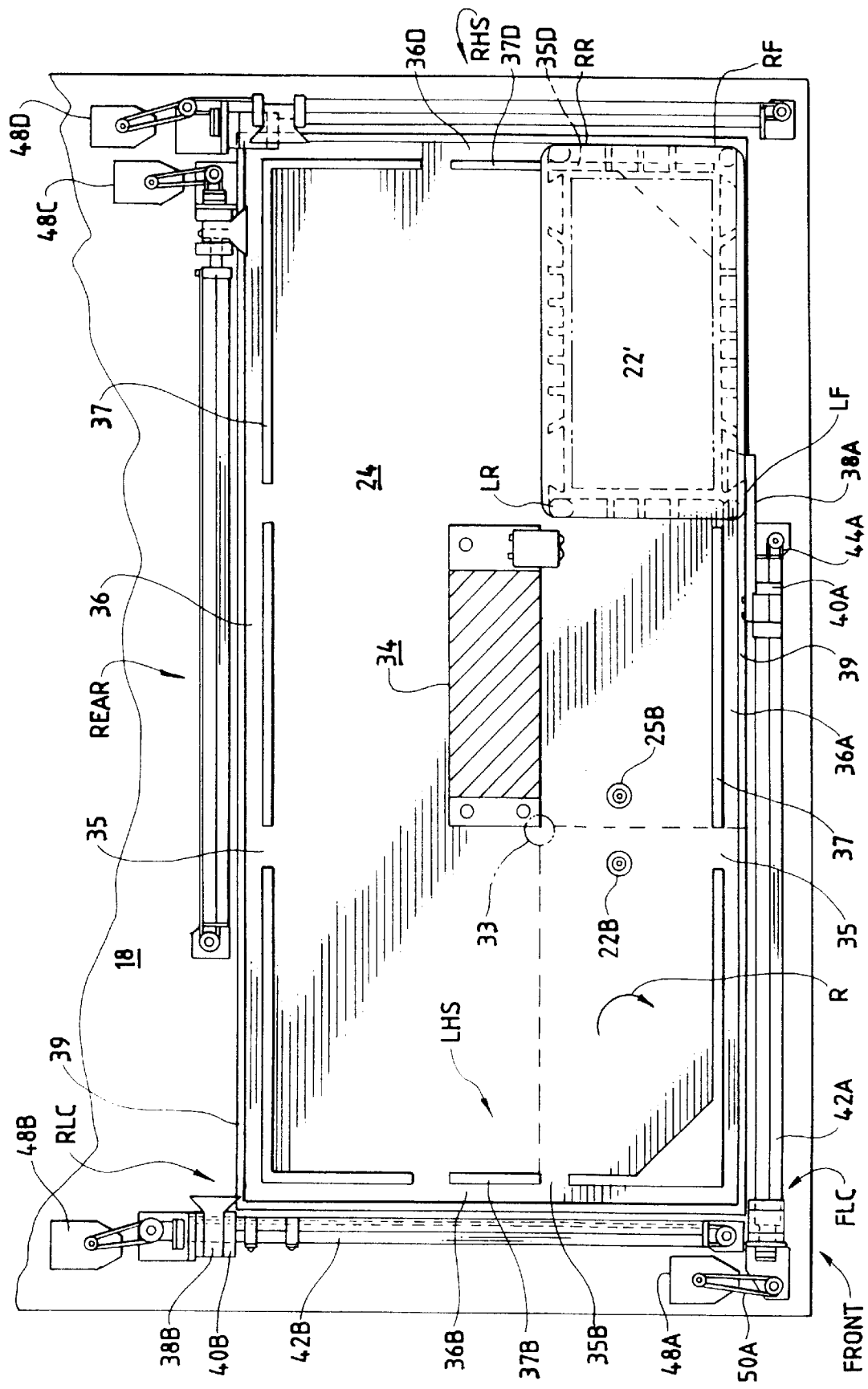
FIG. 4 is a plan view of the base pan of FIGS. 1–3.
Figure 5:
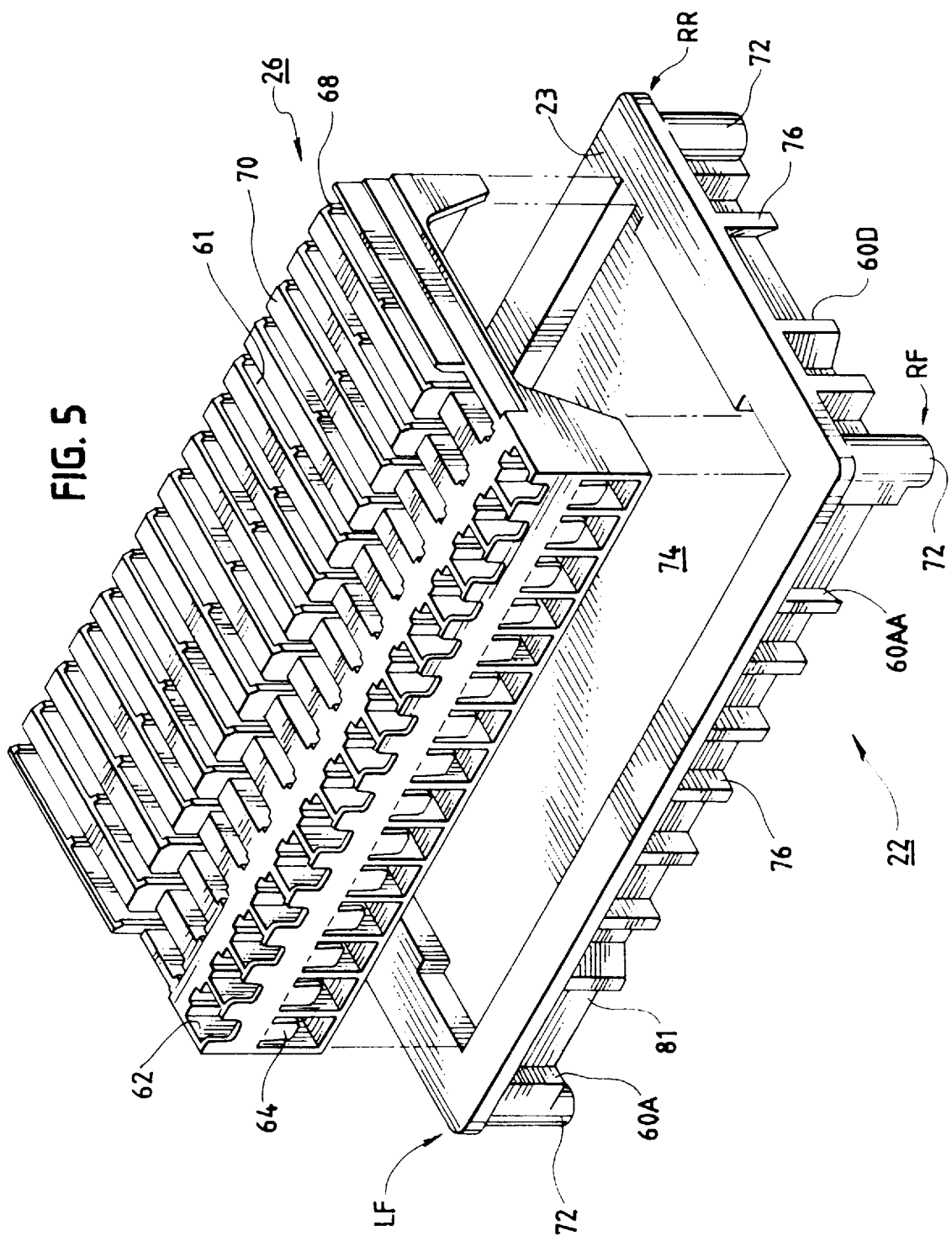
FIG. 5 is a detailed perspective view of the boat and cassette of FIGS. 1–3.
Figure 6:
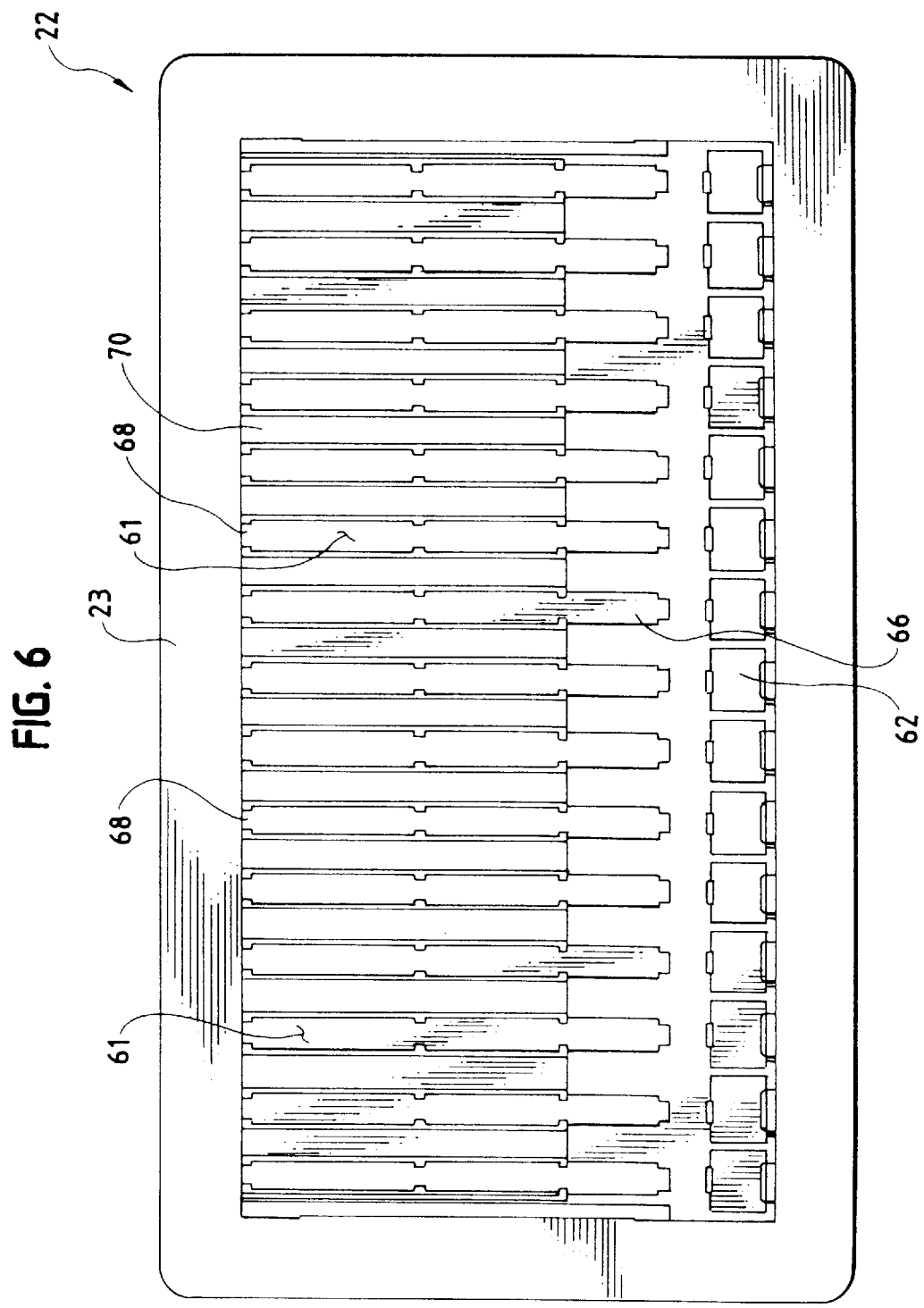
FIG. 6 is a plan view of the cassette and boat of FIG. 5 in an assembled condition.
Figure 10:
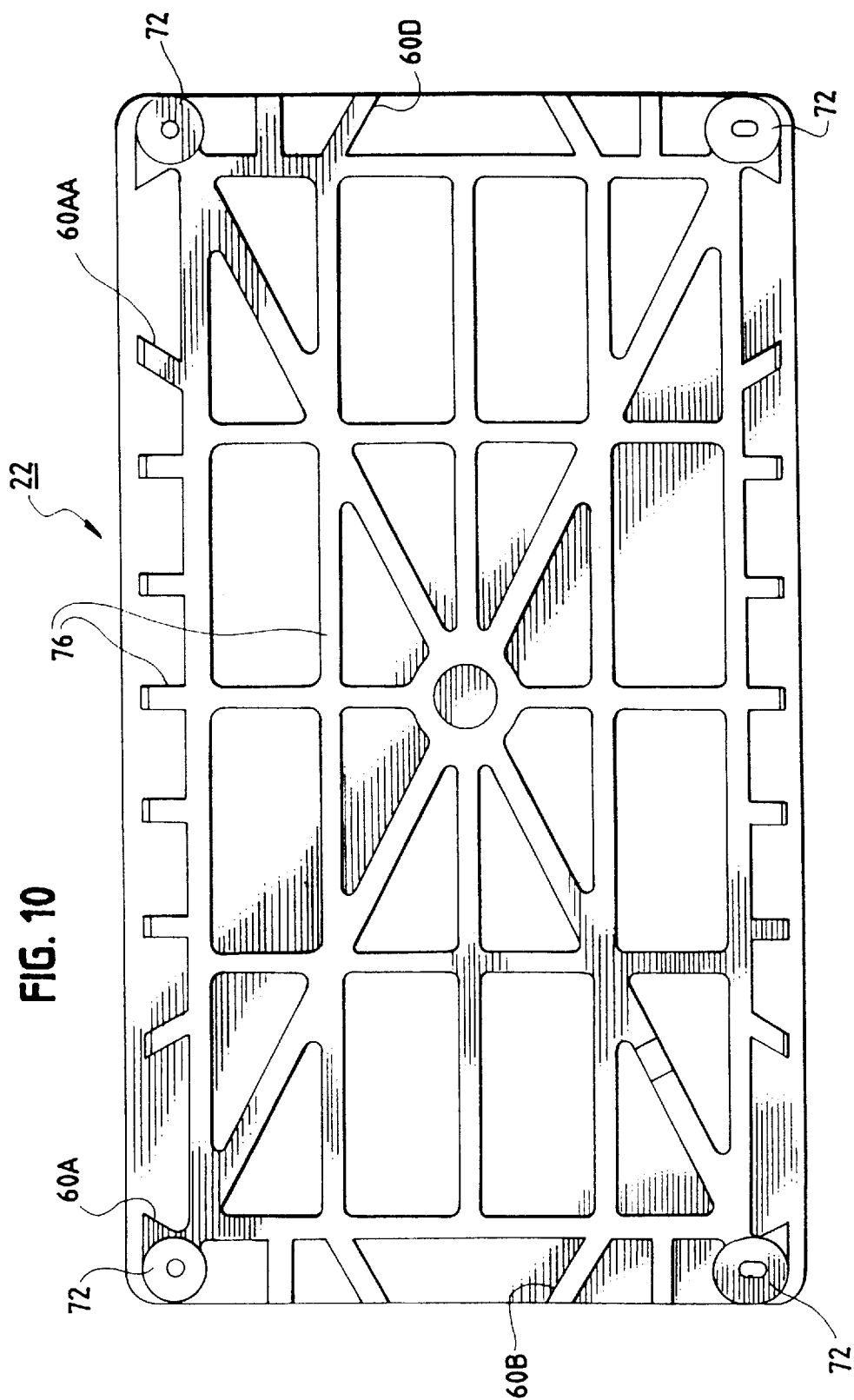
FIG. 10 is a bottom plan view of the boat of FIGS. 1 and 5–9.

Referring to FIGS. 3–5, the boat 22 has four downwardly depending feet 72 (FIGS. 5, 10) which fit in a pattern of track sections comprising grooves 36 formed between a set of raised ridges 37 and a raised rim 39 extending around the perimeter of the base pan 24. The grooves 36 help prevent any rotation of the boat 22 as the boat 22 is pulled over the base pan 24.

When the boat 22 is initially located at the loading station, as shown in FIG. 4, the left front LF and right front RF feet 72 of the boat 22 are positioned in groove 36A, the right rear (RR) foot 72 is in groove 36D, with the RF foot 72 at the intersection of grooves 36A and 36D. A plurality of slots 35 are provided in the raised ridges 37 so as to permit the feet 72 of the boat 22 to move through the ridges 36 as the boat 22 is moved about the base pan 24. For example, slot 35D permits the right rear RR foot 72 to move past raised ridge 37D, and slot 35B permits the left rear LR foot 72 to move past the ridge 37B into the groove 36B.

In order to move the boat 22 clockwise about the base pan, four independent drive systems are provided for moving the boat 22. Each drive system moves the boat 22 in one direction along one of the four sides of the base pan 24. Referring now in particular to FIG. 3, a first drive system is provided for moving the boat 22 along the front edge of the base pan 24, and consists of a rotatable shaft 42A having a square cross section, a collar 40A slideably mounted the shaft 42A, a drive belt 44A mounted to the collar for sliding the collar 40A along the shaft 42A, a stepper drive motor 48A driving a belt 50A, and a pulley 52A for moving the drive belt 44A back and forth along the front edge of the base pan, and a second pulley 46A for the drive belt 44A. A paddle 38A is mounted to the collar 40A, and is provided for engaging a complimentary surface of the boat 22 such that when the drive motor 48A is operative to move the belt 44A such that the collar 40A is moved to the left along the shaft 42A, the paddle 38A drags the boat 22 to the left across the base pan 24.

A shaft rotate motor 54A is also provided with an associated belt and pulley (not shown) for rotation of the shaft 42A by an angle of 90 degrees. When the shaft rotate motor 54A rotates the shaft 42A such that the head of the paddle 38A is in a horizontal position in the direction of the boat 22, the paddle 38A is in a position to engage a complimentary surface on the side of the boat 22 so as to drag the boat 22 as the paddle 38A and collar 40A are moved along the shaft 42A. When the boat has reached the end of its travel along the front edge of the base pan 24, the shaft rotate motor 54A rotates the shaft 42A 90 degrees in a direction such that the paddle 38A is rotated upwards away from the side of the boat 22, thereby disengaging the paddle 38A from the boat 22.

Referring now in particular to FIG. 11, the paddle 38A and its engagement with a complimentary engaging surface 60A of the boat 22 is shown in greater detail. FIG. 11 shows the boat 22 and paddle 38A in position for movement of the boat 22 to the left along the front side of the base pan 24. The movement of the belt 44A by motor 48A causes the collar 40A to slide along the shaft 42A, to the left (or to the right) depending on whether the motor 48A is operated in a forward or reverse direction. The head H of the paddle 38A pulls the boat such that the left front foot LF slides along the groove 36A and maintains alignment of the boat 22 relative to the base pan 24. From FIG. 11, it can be seen that the complimentary paddle engaging surface PE comprises a surface oriented at an acute angle relative to the long axis of the shaft 42A. The surface PE lies in a vertical plane passing through the base pan. The acute angle is preferably between 30 and 60 degrees. The other drive systems around the periphery of the base pan work in essentially the same manner.

Specifically, each of the other three drive systems in the sample positioning system 100 is functionally equivalent to the drive system described above for the front edge of the base pan 24, and each is composed of like components. For example, the left hand side LHS drive system has a shaft 42B, collar 40B with attached paddle 38B, drive belt motor 48B, shaft rotation motor 54B etc. Like components for the rear edge of the base pan include a rotatable shaft 42C, belt drive motor 48C, etc. Similarly, the right hand side (RHS) drive system has a rotatable shaft 42D, collar 40D and attached paddle 38D, etc.

FIG. 12 is a sectional view of the collar and shaft of FIG. 11, showing the rotation of the paddle into and out of engagement with the side of the boat 22. This rotation is accomplished by the operation of the shaft rotation motor 54A of FIG. 3 and the movement of its associated belt and pulleys. The collar 40A has a low-friction lining L surrounding the shaft 42A, which reduces the torque on the drive motor for the belt 44D.

FIG. 13 is a perspective view of the fourth drive system that operates to pull the boat 22 along the right hand side of the base pan 24. The drive system includes a collar 40D that slides along the square shaft 42D, and a paddle 38D. The pulley 52D for the drive motor 48D (see FIG. 3) operates to move the belt 44D back and forth, sliding the collar 40D along the shaft 42D. The rotation belt RB for the shaft rotation motor 54D (FIG. 3) serves to rotate the shaft 42D, thereby permitting the paddle 38D to rotate into and out of engagement with the side of the boat 22.

From FIG. 3, it can be seen that after the front drive paddle 38A has slid the boat 22 all the way to the extreme left hand side of the base pan 24, the shaft rotate motor 54A rotates the shaft 42A such that paddle 38A is rotated out of engagement with the boat 22. At this time, the drive motor 54A may then move the paddle 38A all the way to the end of the shaft 42A adjacent to the pulley 46A, so as to enable the paddle to engage another boat. Meanwhile, the drive motor 48B will have moved the LHS paddle 38B to the end of the shaft 42B so as to engage the boat 22 at the left front corner of the base pan 24. The LHS drive motor 48B and paddle 42B enable the boat 22 to be moved along the LHS of the base pan 24 to the vacuum station 400 (FIGS. 1 and 2), or to any other station that may be positioned above the base pan 24 on the LHS of the base pan 24.

Referring in particular to FIG. 4, it is important that when the boat 22 is slid along the LHS of the base pan from its position 22B at the front left corner (FLC) to the rear left corner (RLC), the boat not undergo any substantial rotation, indicated by the arrow R. Substantial rotation would cause the right rear corner RR of the boat 22 to bind at the corner 33 of the center mount 34. While the groove 36B is helpful in preventing rotation, it has been found after experimentation that making corner 33 a sharp corner prevents the binding. The sharp corner immediately forces the boat 22 to maintain alignment in the groove 36B as the boat is moved away from the front left corner FLC as the drive system moves the boat 22 along the left hand side LHS of the base pan 24.

After the vacuum loading test samples into the cards 28 is complete, the LHS drive system moves the boat to the left rear corner of the base pan, and the rear drive system 38C, 40C, 42C, etc. takes over. The rear drive system 38C, 40C, 42C etc. moves the boat 22 into position for loading of the cards one at a time into the carousel of the incubation station. After the rear drive system as moved the boat 22 across the rear of the base pan 24 to the right rear corner of the base pan 24, the RHS drive system 38D, 40D, 42D, etc. takes over to move the boat 22 along the RHS of the base pan.

Since the four drive systems move a boat 22 independently from each other, it is possible for a plurality of boats 22 (e.g., four) to be processed simultaneously in the machine 20. In order to accommodate four boats on the base pan 24 after the cards in the boats have been loaded into the carousel, it may be necessary to advance the first boat to be processed along the front edge of the base pan to the left in order to avoid a jam of boats at the RHS of the base pan and at the loading station 22' (FIG. 4). It may also be necessary to permit the boats to be moved in a counter clockwise direction if for some reason the boats 22 are not positioned exactly where they need to be for the processing of the cards 28 by the various stations. A further possibility is to provide a separate exit station on the rear or RHS of the base pan for boats 22 that have been processed.

The base pan 24 is preferably made out of a low friction and low wear material such as structural foam. Drain holes 25A, 25B are provided on the bottom of the base pan 24 for allowing any spilled fluids on the base pan to be carried out of the machine 20.

An electronic control system for the motors of the test sample positioning system 100 is not shown in the Figures, but can be readily developed from the above description in accordance with well known techniques by those of ordinary skill in the art.

Boat 22 and Cassette 24 Detailed Description

In the preferred embodiment of the invention, the boat 22 is not rotated during its cycle of movement around the machine, and hence the general orientation of the boat 22 is unchanged. Since the boat is moved along four sides of a rectangle in the preferred embodiment, the boat 22 is preferably given a rectangular shape with four sides, each side having a complimentary surface for engaging one of the four paddles 38A–D in the drive system.

The boat 22 and cassette 26 are shown in several views in FIGS. 5–8. The boat and cassette are separate units in the preferred embodiment, with the boat 22 typically remaining in the machine 20 after processing of the cards in the cassette 26 (except for removal for cleaning). The cassette 26 is loaded with cards 28 and test tubes 30 off line, and placed in the machine 20 by a technician at the start of the entire processing procedure. In an alternative embodiment, the boat and cassette could be an integral unitary sample holder that is removed from the machine 20 for loading with cards and test tubes, and placed in to the loading station of the machine for subsequent processing.

Referring to FIGS. 5–8, the boat 22 has a paddle engaging surface 60A which is slanted at an angle relative to the side wall 81 of the boat 22. This planar surface 60A is engaged with a complimentary planar angled surface of the head of the paddle 38A as the paddle slides the boat over the front side of the base pan 24. A second angled engaging surface 60AA is provided, which allows the paddle 38A (FIG. 3) to engage a second surface on the boat 22. This second engaging surface 60AA reduces the collar travel on the shaft 42A needed to move the boat 22 to the extreme front left corner of the base pan 24. The paddle 38A may be rotated out of engagement with surface 60A, moved down the shaft to a position adjacent to surface 60AA, and rotated back into engagement with surface 60AA.

The right hand side of the boat 22 has a surface 60D that is engaged by the paddle 38D when the paddle 38D moves the boat along the right hand side of the base pan 24. Similar engaging surfaces are provided on the rear and left hand sides of the boat 22.

The cassette 26 has a plurality of slots 61 for sample cards 28 (FIG. 1), each of which is adjacent to a test tube holding slot 62 securely retaining a test tube. A tang 64 or other suitable resilient member extends inwardly in the test tube holding slot 62 and prevents the test tubes from moving in the slot 62. The card slots 61 are separated from each other by a wall 70. The slots 61 are given a dimension so as to permit a slight amount of fore and aft movement of the sample cards between adjacent walls 70. The walls 70 extend only about a third of the way up the cards 28, permitting fore and aft rocking motion of the cards by the separation device 94 (see FIG. 1), allowing a bar code reader to read bar codes placed at the top of the cards.

The cards 28 rest on the floor 66 of the slots 61. An open side 68 in the slots permits the cards to be slid out of the cassette 26 into the incubation station 600 (FIG. 1).

Referring to FIG. 5, the boat 22 has a flat floor 74 which contains any spills from the test tubes. The floor 74 is given a shape so as to snugly receive the cassette 26 when the cassette 26 is loaded into the boat 22.

The boat 22 has a substantially flat top planar surface 23 that is supported by a plurality of reinforcing ribs 76 along the sides and bottom of the boat 22. The surface 23 sealingly engages the bottom surface of the vacuum chamber 402 (FIG. 2). The ribs 76 help the boat 22 bear the compressive forces placed on the peripheral sealing surface 23 of the boat 22 by the chamber 402.

Figure 9:
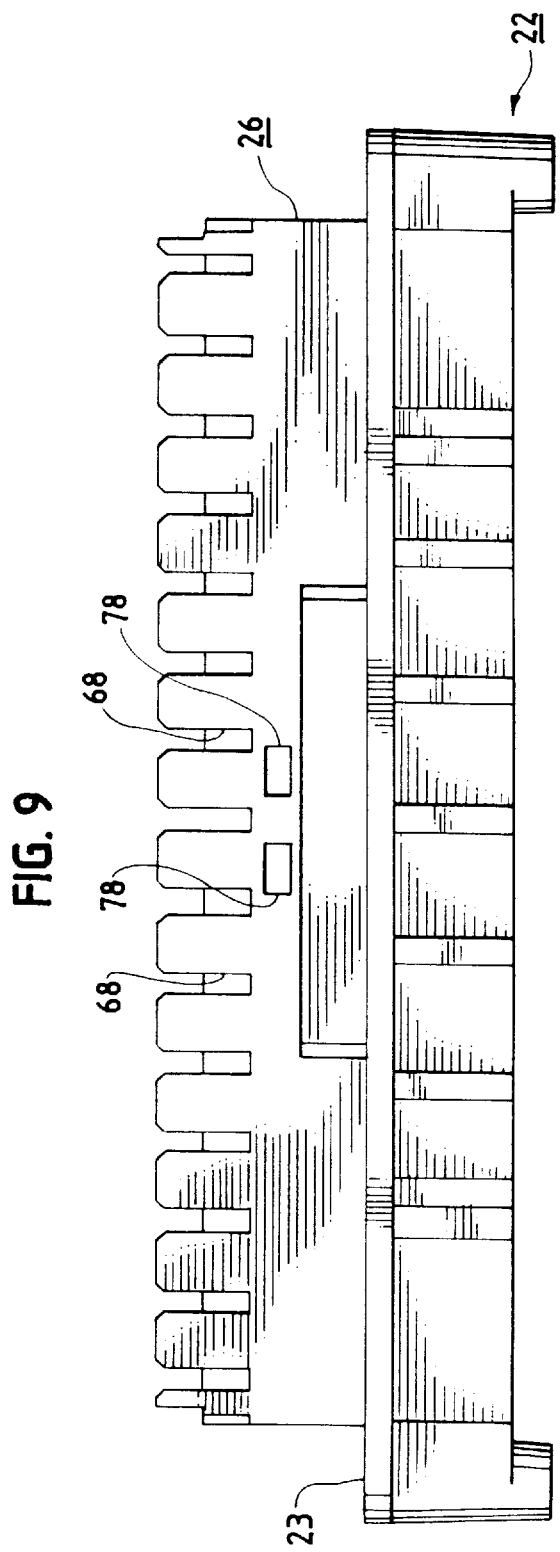
FIG. 9 is a side view of the cassette and boat of FIG. 5, as seen from the opposite side of FIG. 7, showing the apertures in the cassette that receive touch memory buttons that store information as to the cards carried by the cassette.

Referring to FIG. 9, a pair of apertures 78 are provided in the rear of the cassette 26 which receive touch buttons (not shown). The touch buttons identify the contents of the cards 28 loaded into the cassette 26. This information is then read by touch button readers 84 mounted to the center mount 34 of the machine 20 (see FIG. 1). Preferably, a stand-alone cassette identification station is provided for the machine 20. The station has a computer terminal and touch button contacts that load information as to the cards for the cassette onto the touch buttons placed in the touch button apertures 78.

From the foregoing, persons of ordinary skill in the art will appreciate that many variations may be made to the mechanical details of the preferred embodiments without departure from the true spirit and scope of the invention. For example, the details of the drive system may change depending on the shape and size of the boat, the geometry of the testing machine, and the type of stations that are employed in the machine. The configuration of the boat and base pan may also dictate the shape of the paddles and the guide rails in the base pan. The true spirit and scope of the invention is defined by the appended claims, to be interpreted in light of the foregoing.

We claim:

1. A system for moving a sample holder within a machine, the sample holder having first and second side panels, comprising:
   a base pan having a first side region and an adjacent second side region, said sample holder placed on and moved about said machine on said base pan;
   a first drive system engageable with said first side panel of said sample holder for moving said sample holder in a forward direction along said base pan aligned with said first side region, said first drive system positioned adjacent to said first side region of said base pan and operative, when engaged with said first side panel of said sample holder, to pull said sample holder over said base pan wherein said sample holder slides over said base pan;
   a second drive system engageable with said second side panel of said sample holder for moving said sample holder in a forward direction along said base pan aligned with said second side region, said second drive system positioned adjacent to said second side region of said base pan and operative, when engaged with said second side panel of said sample holder, to pull said sample holder over said base pan wherein said sample holder slides over said base pan;
   wherein said first and second drive systems are independently operable so as to move said sample holder about said base pan sequentially along said first and second side regions and without requiring the presence of other sample holders on said base pan to effectuate the movement of said sample holder about said base pan in said forward direction.

2. The system of claim 1, wherein said first and second drive systems each comprise a paddle engaging said first and second side panels of said sample holder, respectively, said paddle slideably mounted to a shaft, the shaft axially fixed with respect to said base ban and extending parallel to said first and second side regions of said base pan, respectively.

3. A system for moving a sample holder within a machine, the sample holder having first and second side panels, comprising:
   a base pan having first and second side regions, said sample holder placed on and moved about said machine on said base pan;
   a first drive system engageable with said first side panel of said sample holder for moving said sample holder in a forward direction along said base pan aligned with said first side region, said first drive system positioned adjacent to said first side region of said base pan;
   a second drive system engageable with said second side panel of said sample holder for moving said sample holder in a forward direction along said base pan aligned with said second side region, said second drive system positioned adjacent to said second side region of said base pan;
   wherein said first and second drive systems are independently operable so as to move said sample holder about said base pan sequentially along said first and second side regions and without requiring the presence of other sample holders on said base pan to effectuate the movement of said sample holder about said base pan in said forward direction,
   wherein said first and second drive systems each comprise a paddle engaging said first and second side panels of said sample holder, respectively, said paddle slideably mounted to a shaft, the shaft axially fixed with respect to said base ban and extending parallel to said first and second side regions of said base pan, respectively, and
   wherein said shaft and paddle of each of said first and second drive systems are rotatable about an axis relative to said base pan as a unit to allow said paddle to be rotated into and out of engagement with said first and second side panels of said sample holder, respectively.

4. The system of claim 3, wherein said paddle of each of said first and second drive systems are operative, when engaged with said first and second side panels of said sample holder, respectively, to pull said sample holder along said base pan wherein said sample holder slides over said base pan.

5. The system of claim 1, wherein said base pan further comprises at least one raised ridge positioned parallel to and spaced apart from said first and second side regions of said base pan to thereby define a track section receiving a plurality of feet depending from said sample holder to help guide said sample holder as said sample holder is pulled by said first and second drive systems over said base pan.

6. The system of claim 3, wherein said base pan further comprises at least one raised ridge positioned parallel to and spaced apart from said first and second side regions of said base pan to thereby define a track section receiving a plurality feet depending from said sample holder to help guide said sample holder as said sample holder is pulled by said first and second drive systems over said base pan.

* * * * *